United States Patent [19]

McLennan et al.

[11] Patent Number: 4,820,428

[45] Date of Patent: Apr. 11, 1989

[54] ANTIMICROBIAL COMPOSITIONS AND METHODS

[75] Inventors: John M. McLennan, Calgary, Canada; Keith D. Brunt, East Bridgford; Walter G. Guthrie, East Leake, both of England

[73] Assignees: Oilfield Speciality Products Manufacturing Ltd., of Canada, Canada; The Boots Company, plc, of England, England; a part interest

[21] Appl. No.: 933,548

[22] Filed: Nov. 21, 1986

[30] Foreign Application Priority Data

Nov. 21, 1985 [GB] United Kingdom ............... 8528729

[51] Int. Cl.$^4$ ..................... E21B 41/02; E21B 43/00
[52] U.S. Cl. ............................. 252/8.551; 252/8.555; 514/727
[58] Field of Search .............. 252/8.551, 8.554, 8.555, 252/8.552; 514/727

[56] References Cited

U.S. PATENT DOCUMENTS

| | | | |
|---|---|---|---|
| 2,599,384 | 6/1952 | Gross et al. | 252/8.555 |
| 2,637,536 | 5/1953 | Dement | 252/363.5 X |
| 2,824,059 | 2/1958 | Chamot | 252/8.555 |
| 2,891,009 | 6/1959 | Case | 252/8.555 |
| 2,970,959 | 2/1961 | Jones | 252/8.552 |
| 3,001,936 | 9/1961 | Bennett et al. | 252/8.554 |
| 3,024,192 | 3/1962 | Bennett et al. | 252/8.554 |
| 3,076,508 | 2/1963 | Lissant | 252/8.552 X |
| 3,275,552 | 9/1966 | Kern et al. | 252/8.552 |
| 3,531,409 | 9/1970 | Seffens et al. | 252/8.552 X |
| 4,113,444 | 9/1978 | Bunting | 44/72 |

Primary Examiner—Herbert B. Guynn
Attorney, Agent, or Firm—Jacobs & Jacobs

[57] ABSTRACT

Novel solid antibacterial compositions suitable for use in an oil or gas well comprise at least 50% by weight of a solid antibacterial nitroalkanol compound active against sulphate-reducing bacteria and a carrier, the composition having a density of at least 1.2 g/cm$^3$ and being adapted to dissolve, disintegrate or disperse in water but not in oil. A preferred antimicrobial compound is 2-bromo-2-nitropropane-1,3-diol. The antibacterial compositions are introduced into the aqueous layer in the sump at the bottom of the collecting system of the oil or gas well. This inhibits corrosion in the metal work of the oil or gas well, for example the pipe lines of the collecting system.

11 Claims, No Drawings

ANTIMICROBIAL COMPOSITIONS AND METHODS

This invention relates to the production of oil and gas from wells. In particular it relates to novel compositions and methods for the inhibition of bacterial growth in an oil or gas well which, if not controlled, causes serious corrosion in pipelines and the like and may adversely effect the quality of the oil or gas.

It is known that corrosion occurs in, for example, the pipelines from an oil well due to the production of acids associated with the growth of bacterial colonies, especially colonies of sulphate-reducing bacteria. These colonies develop in water in the presence of oil and may infect the whole of the well and the gathering system. A similar problem occurs in the collection of gas. Droplets of water are formed along the collecting system for the gas and are deposited on the walls of, e.g. the pipelines where colonies of the bacteria develop and give rise to corrosion.

At the present time various methods of using antibacterial compounds to inhibit bacterial growth in oil and gas wells are employed.

For example, in oil wells in which water flooding operations are used, an antibacterial compound is often incorporated in the water used for the flooding operations. In another method used in both oil and gas wells, well squeeze treatments are used in which water or an aqueous fluid containing an antibacterial compound is forced under pressure down the well and into the oil-bearing strata. In a further method used in both oil and gas wells, an antibacterial compound is injected into the collecting system downstream from the well head.

It will be appreciated by those skilled in the art that an antibacterial compound used in the above methods of treatment should have a high level of antibacterial activity against sulphate-reducing bacteria, for examlple, *Desulphovibrio desulphuricans.* The antibacterial compound bronopol (2-bromo-2-nitropropane-1,3-diol) is one such compound and it has been used in the methods of treatment described above.

However known compositions and methods of using antibacterial compounds to inhibit bacterial growth are not entirely satisfactory in terms of both efficacy and convenience and use and there is a need for improved compositions and methods.

Oil and gas wells have a collecting system which passes underground, usually vertically and often for hundreds or even thousands of feet. At the bottom of this collecting system there is usually a sump which generally contains an aqueous layer. The present invention is concerned with inhibiting bacterial growth in this aqueous layer and hence inhibiting the spread of bacterial infection to the collecting system itself.

The present invention is based on the discovery that solid antibacterial nitroalkanols, e.g. nitroalkanols of formula I as hereinafter disclosed, and especially bronopol, can be formulated as a solid composition comprising at least 50% solid antibacterial nitroalkanol and having a density of at least 1.2 g/cm$^3$, and can be readily adapted to dissolve, disintegrate or disperse in water. Furthermore, this composition is not affected to any significant extent by oil and so the composition may be introduced into the aqueous layer at the bottom of the sump simply by causing it to drop through the oil layer.

Accordingly the present invention provides a solid antibacterial composition comprising at least 50% by weight of a solid antibacterial nitroalkanol effective against sulphate-reducing bacteria and a carrier, the composition having a density of at least 1.2 g/cm$^3$ and being adapted to dissolve, disintegrate or disperse in water but not in oil.

The antibacterial compound can be delivered to the aqueous layer in the sump by insertion of a solid antibacterial composition according to the invention at the well head. In passing down to the sump it must either pass through a layer of oil or a volume of gas under pressure. The antibacterial composition must be in such a form as to withstand the pressure of the gas or the hydrostatic pressure of the oil. It will also be appreciated that the antibacterial compositions should dissolve, disintegrate or disperse in water but not in oil.

The solid antibacterial compound used in the compositions and method of the present invention must be active against sulphate-reducing bacteria. In addition, it is preferably water-soluble and preferentially partitions in the aqueous phase of a water/oil system. Furthermore it preferably has a rapid onset of action and its antibacterial activity is preferably not significantly diminished in the presence of brines.

Preferred antibacterial nitroalkanols for use in accordance with the present invention are nitroalkanols of formula I

wherein $R_1$ represents hydrogen or an alkyl group and $R_3$ represents hydrogen or $R_1$ and $R_3$ together with the shared carbon atom from a cycloalkyl group; $R_2$ represents hydrogen, an alkyl group, chlorine, bromine or the group —$CR_5(OH)R_4$ wherein $R_4$ represents hydrogen or an alkyl group and $R_5$ represents hydrogen or $R_4$ and $R_5$ together with the shared carbon atom form a cycloalkyl group; and X represents a chlorine or bromine atom.

Preferred alkyl groups include those having from 1 to 12 carbon atoms, more preferably 1 to 6 carbon atoms, especially 1 to 4 carbon atoms. Suitable alkyl groups include methyl, ethyl, and straight or branched propyl and butyl.

A particularly favoured sub-class of these nitroalkanols are nitroalkanols of formula II

wherein $R_1$ represents hydrogen or a $C_{1-12}$ alkyl group and $R_3$ represents hydrogen or $R_1$ and $R_3$ together with the shared carbon atom form a $C_{5-7}$ cycloalkyl group; and $R_2$ represents hydrogen, a methyl group, an ethyl group, a hydroxymethyl group or bromine.

Preferred alkyl groups include those having 1 to 6 carbon atoms, more preferably 1 to 4 carbon atoms. Suitable alkyl groups include methyl, ethyl, and straight or branched propyl and butyl.

Examples of nitroalkanols which may be employed include those of the following formulae:

A  $C_2H_5CH(OH)CHBrNO_2$

-continued
B CH₂(OH)CBrNO₂CH₂OH
C nC₃H₇CH(OH)CHBrNO₂
D CH₃CH(OH)CBrNO₂CH₂OH
E CH₃CH(OH)CHBrNO₂
F (CH₃)₂CHCH(OH)CBr₂NO₂
G nC₅H₁₁CH(OH)CHBrNO₂
H nC₆H₁₃CH(OH)CHBrNO₂
I CH₂(OH)CNO₂BrCH₃
J CH₃CH(OH)CBr₂NO₂
K C₁₁H₂₃CH(OH)CHBrNO₂
L CH₂(OH)CHBrNO₂
M nC₄H₉CH(OH)CHBrNO₂
N C₂H₅CH(OH)CNO₂BrCH₃
O CH₂(OH)CNO₂BrC₂H₅
P C₂H₅CH(OH)CBr₂NO₂

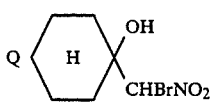

R (CH₃)₂CHCBrNO₂CH(OH)CH₃
S CH₃CH(OH)CBrNO₂C(OH)(CH₃)₂
T (CH₃)₂CHCH(OH)CHBrNO₂

Of these compounds 2-bromo-2-nitropropane-1,3-diol (sold under the Trademark "Bronopol") is especially preferred.

The solid formulations of the present invention, for example solid blocks, contain at least 50% w/w Bronopol. Preferably they contain at least 60% w/w Bronopol, more preferably at least 70% w/w bronopol. For some applications at least 80% w/w Bronopol is preferred.

It will be appreciated that the density of the antibacterial compositions should be such that the solid compositions of the present invention will sink through the gas or oil in the collecting system at an acceptable rate. In order to achieve this the composition must have a density of at least 1.2 g/cm³. The density of the antibacterial compositions of the present invention is more usually at least 1.3 g/cm³ and often at least 1.4 g/cm³. More preferably the density is at least 1.5 g/cm³, especially at least 1.6 g/cm³. Where the oil well produces a heavy oil, a density of at least 1.7 g/cm³ or 1.8 g/cm³ may be preferred.

Preferred compositions of the present invention are solid compositions comprising an effervescent couple which effervesces in the presence of water, for example an effervescent couple which produces carbon dioxide in the presence of water.

One component of the effervescent couple is suitably an acid, for example a solid acid such as sulphamic acid, citric acid, tartaric acid or adipic acid. The other component of the effervescent couple is suitably a metal carbonate or bicarbonate, for example sodium bicarbonate, sodium carbonate, calcium carbonate, barium carbonate, zinc carbonate, nickel carbonate, lead carbonate or cupric carbonate.

Such effervescent compositions of the present invention are very effective in inhibiting bacterial growth in the aqueous layer present in the sump of an oil or gas well.

If desired one or more surfactants may be incorporated in the compositions of the present invention to facilitate contact between the antimicrobial compound and the bacteria which are present in the aqueous layer in the sump, in which oil or gas is also usually present.

Weighting agents may be incorporated in the solid compositions of the present invention to achieve the desired density. Weighting agents are used in the oil and gas industry in drilling and completing muds and are well known, for example sodium bromide, calcium bromide, calcium chloride and barium sulphate and heavy metal carbonates, e.g. lead carbonate and barium carbonate.

The antibacterial compositions of the present invention are in solid form. Such compositions are preferably prepared in the form of solid blocks. A convenient form is a cylindrical block of a suitable size for insertion in the wall head of the collecting system. Thus, for example, a suitable size is often a cylindrical block of diameter about 1.5–5 cm more usually 2–4 cm and length 5–30 cm, more usually 10–25 cm.

Solid formulations of the present invention may be prepared by using a suitable bonding agent, for example cetomacrogol or a suitable polyethyleneglycol, that is solid at ambient temperature but which melts on heating. A hot fluid mixture of the antibacterial compound, weighting agent and molten binding agent is prepared, filled into appropriately sized moulds, and allowed to cool to form solid compositions of the desired shape and size.

Solid formulations of the present invention may also be prepared by compressing a mixture of the antibacterial compound and an aqueous or non-aqueous solution of a suitable binding agent in a suitable die, and then allowing the resulting compressed compositions to dry. Suitable binding agents include, for example, polyvinylpyrrolidone, sodium alginate, microcrystalline cellulose and cellulose ethers such as Methocel K4M and Methocel K15M (Methocel is a Trade Mark). Methocel cellulose ethers are available from the Dow Chemical Company.

Solid formulations of the present invention may also be prepared using dry compression methods and tabletting excipients known in the art of tablet making.

The present invention also provides a method of inhibiting the growth of bacteria in an oil or gas well having a collecting system and a sump at the bottom of the collecting system containing an aqueous layer which comprises introducing a solid antibacterial composition comprising at least 50% by weight of a solid antibacterial nitroalkanol effective against sulphate-reducing bacteria and a carrier, the composition having a density of at least 1.2 g/cm³ and being adapted to dissolve, disintegrate or disperse in water but not in oil into the aqueous layer in the sump.

Suitably the antibacterial nitroalkanol is introduced into the aqueous layer in an amount sufficient to give a concentration greater than 5 ppm, preferably greater than 50 ppm, in the aqueous layer.

This treatment provides a method of inhibiting corrosion in the metal work of an oil or gas well, for example the pipelines in the collecting system.

The following non-limitative Examples illustrate the invention.

EXAMPLE 1

Cylindrical blocks containing Bronopol were prepared from the following ingredients.

| Ingredient | % w/w |
|---|---|
| Bronopol | 75.0 |
| Cetomacrogol 1000 BP | 5.0 |

| Ingredient | % w/w |
| --- | --- |
| Soprophor S25 | 2.0 |
| Cupric carbonate | 7.0 |
| Citric acid | 11.0 |

Soprophor S25 is a nonionic surfactant available from Rhone-Poulenc (UK) Ltd. It is a condensate of tristyrylphenol and ethylene oxide.

The cetomacrogol and Soprophor S25 were blended together at a temperature of about 50° C. The temperature of the mixture was maintained at this level while the cupric carbonate and citric acid were added and blended into the mixture. Finally the Bronopol was added and the ingredients were thoroughly mixed. The warm molten mass was filled into a cylindical mould and allowed to cool to give a cylindrical block of length 3.7 cm, diameter 2 cm. and density 1.72 g/cm$^3$. The block was cut halfway along its length and one half of the block was dropped into gently stirred water (800 ml) at 40°-42° C. The block effervesced and completely dissolved within 4 minutes.

EXAMPLE 2

A mixture of Bronopol (20 g) and 1 g aqueous solution containing Methocel K15M (2% w/v) and propylene glycol (2% w/v) was prepared. The resulting pasty mass was compressed in a die to give a solid block which was allowed to dry in the air. The block had a density of 1.6 g/cm$^3$ and was approximately 2 cm in diameter and 4.7 cm in length. The resulting block was dropped into gently stirred water (1600 ml) at 40°-42° C. The block completely dissolved within 5 minutes.

EXAMPLE 3

A mixture of Bronopol (18 g), 1 g sodium carbonate, 1 g citric acid and 1 g methanolic solution containing polyvinylpyrrolidone K20-35 (2% w/v) was prepared. The resulting pasty mass was compressed in a die to give a solid block which was allowed to dry in the air. The block had a density of approximately 1.6 g/cm$^3$ and was approximately 2 cm in diameter and 4.7 cm in length. The resulting block was dropped into gently stirred water (1600 ml) at 40°-42° C. The block completely dissolved within 2 minutes 9 seconds.

EXAMPLE 4

The ingredients were combined in the same manner as described in Example 3 using 2 g of a solution of polyvinylpyrrolidone K20-35 in isopropyl alcohol in replacement for the methanolic solution of polyvinylpyrrolidone. In the dissolution test described in Example 3, the block completely dissolved in 5 minutes 9 seconds.

EXAMPLE 5

The ingredients were combined in the same manner as described in Example 3 using 2 g of a solution of polyvinylpyrrolidone K90 in isopropyl alcohol in replacement for the methanolic solution of polyvinylpyrrolidone. In the dissolution test described in Example 3, the block completely dissolved in 3 minutes 20 seconds.

EXAMPLE 6

In a similar manner to that described in Example 3 a mixture of Bronopol (20 g) and 2 g methanolic solution containing polyvinylpyrrolidone K20-35 (2% w/v) was prepared. In the dissolution test described in Example 3, the block completely dissolved in 3 minutes 30 seconds.

EXAMPLE 7

The dissolution characteristics of solid blocks formulated in accordance with the invention were investigated.

Slug A comprised 90% w/v Bronopol and 10% w/v Methocel K4M 2% gel.

Slug B comprised 85% w/v Bronopol, 10% w/v sorbitol and 5% w/v Methocel K4M 2% gel with 2% propylene glycol.

5 g aliquots of slugs A and B were dosed in a column 3.5 meters high containing approximately 0.20 m oil and approximately 3.4 m of water (corresponding to a volume of approximately 45 dm$^3$). The water temperature in the column was maintained at approximately 35° C. using a steam tracing and left for 48 or 72 hours before sampling. The concentration of Bronopol in parts per million was measured in each sample.

| Sample | 48 hrs (ppm bronopol) | 72 hrs (ppm bronopol) |
| --- | --- | --- |
| Slug A | | |
| Top | 11 | 15 |
| Middle | 11 | 15 |
| Bottom | 1912 | 503 |
| Slug B | | |
| Top | 27 | 44 |
| Middle | 44 | 44 |
| Bottom | 56 | 116 |

EXAMPLE 8

In a similar manner as described in Example 1 there is prepared a solid block in which Bronopol is replaced by the same amount of a nitroalkanol selected from the following:
1. 2-bromo-2-nitro-butan-1-ol
2. 2-bromo-2-nitrobutan-1,3-diol
3. 1-bromo-1-nitro-butan-2-ol
4. 1-bromo-1-nitro-octan-2-ol
5. 1,1-dibromo-3-methyl-1-nitrobutan-2-ol
6. 2-bromo-2-nitro-propan-1-ol
7. 1-bromo-1-nitro-3-methyl-butan-2-ol

We claim:

1. An antibacterial composition in the form of a solid block for the inhibition of bacterial growth in gas and oil wells, consisting essentially of at least 80% by weight of a solid antibacterial nitroalkanol effective against sulphate-reducing bacteria and a binding agent selected from the group consisting of, cetomacrogol, polyethyleneglycol, polyvinylpyrrolidone, sodium alginate, microcrystalline cellulose and a cellulose ether, the composition having a density of at least 1.5 g/cm$^3$, being able to withstand the pressure of the gas or the hydrostatic pressure of the oil and being adapted to dissolve, disintegrate or disperse in water but not in oil.

2. A composition according to claim 1 wherein the nitroalkanol is of the formula I

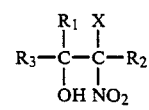

wherein $R_1$ is hydrogen or alkyl and $R_3$ is hydrogen or $R_1$ and $R_3$ together with the shared carbon atom form a cycloalkyl group; $R_2$ is hydrogen, alkyl, chlorine, bromine or the group $-CR_5(OH)R_4$ wherein $R_4$ is hydrogen or alkyl and $R_5$ is hydrogen or $R_4$ and $R_5$ together with the shared carbon atom form a cycloalkyl group; and X is chlorine or bromine.

3. A composition according to claim 1 wherein the nitroalkanol is of the formula II

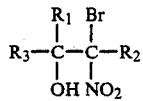

wherein $R_1$ is hydrogen or alkyl of 1 to 12 carbon atoms and $R_3$ is hydrogen or $R_1$ and $R_3$ together with the shared carbon atom form a cycloalkyl group of 5 to 7 carbon atoms; and $R_2$ is hydrogen, methyl, ethyl, hydroxymethyl or bromine.

4. A composition according to claim 3 wherein the nitroalkanol is 2-bromo-2-nitropropane-1,3-diol, 2-bromo-2-nitro-butan-1-ol, 2-bromo-2-nitrobutan-1,3-diol, 1-bromo-1-nitro-butan-2-ol, 1-bromo-1-nitro-octan-2-ol, or 2-bromo-2-nitro-propan-1-ol.

5. A composition according to claim 4 wherein the nitroalkanol is 2-bromo-2-nitropropane-1,3-diol.

6. A composition according to claim 1 which additionally contains an effervescent couple which effervesces in the presence of water.

7. A method of inhibiting the growth of bacteria in an oil or gas well having a collecting system and a sump at the bottom of the collecting system containing an aqueous layer, comprising introducing a composition according to claim 1 into the aqueous layer in the sump.

8. A method according to claim 7 in which the amount of antibacterial nitroalkanol introduced into the aqueous layer is sufficient to give a concentration greater than 5 ppm in the aqueous layer.

9. A method according to claim 7 in which the concentration of antibacterial nitroalkanol in the aqueous layer is at least 50 ppm.

10. A composition according to claim 1 which additionally contains a nonionic surfactant.

11. A composition according to claim 10 wherein the nonionic surfactant is a condensate of tristyrylphenol and ethylene oxide.

* * * * *